United States Patent [19]

Emerson et al.

[11] Patent Number: 5,219,350
[45] Date of Patent: Jun. 15, 1993

[54] MEDICAL INSTRUMENT

[76] Inventors: Clarence A. Emerson, 116 Sunset Blvd.; Dennis L. Riddell, 127 Percival Path, both of Bozeman, Mont. 59715

[21] Appl. No.: 592,997

[22] Filed: Oct. 5, 1990

[51] Int. Cl.$^5$ .............................................. A61F 9/00
[52] U.S. Cl. .................... 606/107; 362/119; 606/162
[58] Field of Search ........... 606/107, 131, 162, 166, 606/167; 362/119, 120

[56] References Cited

U.S. PATENT DOCUMENTS

| | | | |
|---|---|---|---|
| 1,386,309 | 8/1921 | Bingman | 606/162 |
| 1,449,165 | 3/1923 | Cameron | 362/120 |
| 1,597,500 | 8/1926 | Alexander et al. | 606/107 |
| 2,410,257 | 10/1946 | Andrzejewski | 606/107 |
| 2,555,550 | 6/1951 | Krivanek et al. | 606/162 |
| 3,603,782 | 9/1971 | Wortmann | 362/120 |
| 3,655,960 | 4/1972 | Andree | 362/119 |
| 3,743,337 | 7/1973 | Crary | 606/107 |
| 4,137,561 | 1/1979 | Andree | 362/119 |
| 4,542,741 | 9/1985 | Burgin | 362/119 |
| 4,657,012 | 4/1987 | Burgin | 362/119 |

FOREIGN PATENT DOCUMENTS 153896 7/1932 Switzerland .................... 362/119

Primary Examiner—Stephen C. Pellegrino
Assistant Examiner—Ralph A. Lewis
Attorney, Agent, or Firm—Richard C. Conover

[57] ABSTRACT

A first aid instrument for removing slivers from the skin, and foreign material from an eye. The instrument, which furnishes light to a work area, has a variety of interchangeable tools that can be used with the instrument. The instrument has a hollow handle that accommodates a power source for light, a bulb, and a transparent nose. The nose transmits light from the bulb to the tip of the instrument so as to focus light on an area where a tool is being used. The transparent nose also holds the tool in a passageway extending through the nose by virtue of an embedded magnet in the passageway. The tools that fit in the nose include a magnet, a loop, a sharpened pointed tool, and other sharpened cutting tools. The instrument also has a clip-on magnifier which has an adjustable arm so that the clip-on magnifier can be placed in an advantageous position for viewing a workpiece.

1 Claim, 1 Drawing Sheet

MEDICAL INSTRUMENT

BACKGROUND OF THE INVENTION

The present invention relates to a first aid instrument for removing foreign objects from a person's body.

In the past, tools have been developed and used in administering first aid. This became necessary since all small medical problems did not warrant a visit to the doctor. These first aid tools became a middle step between no treatment and treatment by a doctor. The great majority of these tools have been developed for use on exterior parts of the body, for example, on skin, eyes, ears, nose, finger and toe nails, etc.

Some of the first aid tools that were developed are as follows: A magnetic tool for removing steel fragments or steel chips from an eye has been around for many years. The magnet is generally imbedded in a handle for easy use and the protruding end of the magnet is smooth and rounded so it will not injure the eyeball.

A handle with a sharp tool for removing slivers has also been used for years. Sometimes the end is shaped like a needle, but generally it is sharpened by being ground on three sides thereby providing three cutting edges along with the sharp tip. This provides a more versatile tool for skin problems. Other cutting tools or blades in a handle have been used for years for many purposes, for example, for cutting skin, paper, cardboard, wood, plastic, etc.

One of the problems with using all of the above mentioned tools is that the user needs to be able to see exactly what he is doing. Much of the time the available light is not bright enough to use these tools.

SUMMARY OF INVENTION

The present invention relates to a first aid instrument, and more particularly relates to a new instrument for removing slivers from the skin, and foreign material from an eye. The instrument furnishes light for the above purposes. The instrument has a variety of interchangeable tools that can be used with it.

The instrument has a hollow handle that accommodates a power source for light, a bulb, and a nose. The nose not only holds a tool that is being used, but also transmits light from the bulb to the tip of the instrument so as to focus light on a work area. The tools that fit in the nose include a magnet, a loop (monofilament or wire), a sharpened pointed tool, and other sharpened cutting tools.

All of these tools can be held in the nose of the instrument while the light from the batteries and bulb illuminates a work area. The instrument also has a clip-on magnifier which has an adjustable arm that can be placed in an advantageous position for viewing a workpiece.

BRIEF DESCRIPTION OF THE DRAWINGS

In order that the invention may be clearly understood and readily carried into effect, a preferred embodiment of the invention will now be described, by way of example only, with reference to the accompanying drawings wherein.

DESCRIPTION OF A PREFERRED EMBODIMENT

Figure 1:
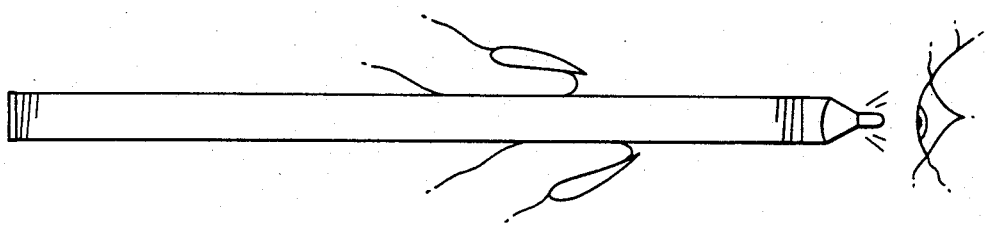
FIG. 1 is an elevational view of the instrument according to the present invention being grasped with a hand of an user.
Figure 2:
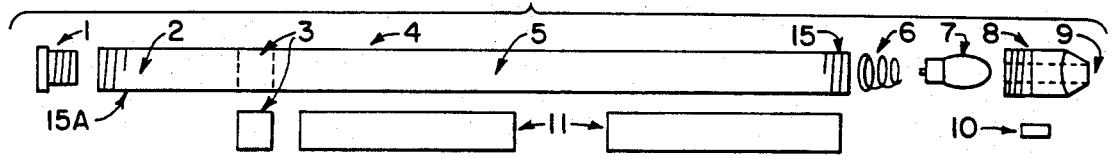
FIG. 2 is an exploded view of the instrument of FIG. 1 with internal batteries illustrated below the instrument.

A preferred embodiment of the illuminated instrument holder is shown in FIG. 1. A knurled cap 1 screws into hollow handle 4 of the instrument on threads 15A to close off both a storage section 2 for tools that are not being used and a compartment 5 for holding batteries 11. A plug 3 is inserted into hollow handle 2 to separate the hollow space inside the handle into two compartments: storage section 2 and battery compartment 5. At one end of the instrument, a spring 6 holds a bulb 7 away from batteries 11. Spring 6 compresses when nose 8 is screwed into female threads 15 which permits bulb 7 to contact batteries 11 to turn the power on and light the bulb.

Nose 8 is made of a transparent material. Nose 8, which has male threads 17 at one end, pushes bulb 7 back against spring 6 when the nose is screwed into female threads 15 on handle 4. Transparent nose 8 also directs light from bulb 7 toward the end of the nose opposite threads 17 to illuminate the area of a workpiece. A hollow passageway 9 passes completely through nose 8. A magnet 10 is sized to fit securely into passageway 9 to plug the passageway. Passageway 9 is also used to hold a tool, described in the next paragraph, which is being held by the instrument.

Figure 3:
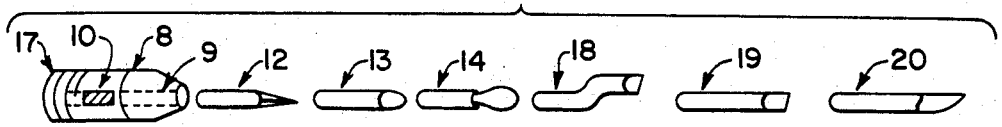
FIG. 3 illustrates various object removal tools for insertion.

As best seen in FIG. 3, nose 8 can accept various tools: Sliver probe 12 has a sharpened point created by grinding three sides to a point to create a three sided needle point. Magnet tool 13 has a bullet shaped tip ground smooth so that is will not scratch an eye. Magnet tool 13 may also have a circular groove adjacent the bullet shaped nose to make it easier for an operator to pull the magnet tool from passageway 9. A loop tool 14 has the ends of a separate wire or monofilament line held securely in the form of a loop. A swivel cutting blade 18 has a sharpened edge. A straight cutting blade 19 has a sharpened chisel point end. A front sharpened straight cutting blade 20 has a sharpened side adjacent the front end of the tool.

Figure 4:
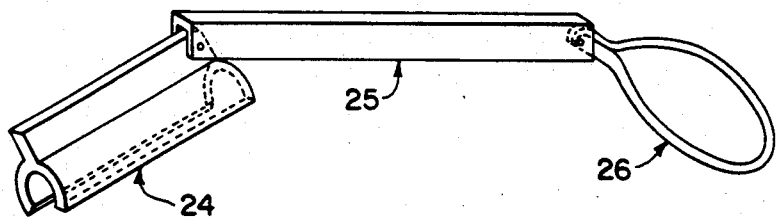
FIG. 4 is an accessory clip-on magnifier which may be attached to the instrument according to the present invention.

A clip-on magnifier is illustrated in FIG. 4. Clip-on magnifier has a clip 24, an arm 25, and a magnifier 26. Clip 24 can be slipped onto handle 4 and can be slid along the handle. Arm 25 and magnifier 26 can be swiveled to place the magnifier in a desirable position.

In operation, an operator holds onto handle 4. Nose 8 is then screwed into handle 4 which pushes against bulb 7, and compresses spring 6. When bulb 7 makes contact with batteries 11, the bulb will light. A desirable tool (selected from those shown in FIG. 3) is inserted into passageway 9 in nose 8 and held there by the action of magnet 10. The remaining tools, those not being used, are then stored in compartment 2 by removing cap 1 and placing them in the compartment.

While the fundamental novel features of the invention have been shown and described, it should be understood that various substitutions, modifications and variations may be made by those skilled in the art without departing from the spirit or scope of the invention.

Accordingly, all such modifications or variations are included in the scope of the invention as defined by the following claim.

What is claimed is:

1. A first aid kit for removing objects from a patient's eye comprising:

an elongated tubular handle having proximal and distal ends, said distal end having an internally threaded surface;

a cylindrical nose member having external threads at a first end for removable rotatable attachment to the internally threaded distal end of said handle and a tapered tip portion at a second opposite end, said nose member including an opening extending between said first and second ends for interchangeable receiving through said tapered second end the shafts of object removal tools, said nose member further including magnetic means for releasably retaining the shafts of object removal tools positioned within said opening and means to transmit light from said first end to said second end;

said handle including illuminating means comprised of a light bulb biased against said nose member first end with a spring means positioned in the handle distal end, said tubular handle further including a portion for holding batteries wherein rotation of the nose member with respect to the handle compresses said spring means and positions said light bulb into electrical contact with batteries adapted to be held within said handle such that the light bulb is energized thereby providing light to said nose member light transmitting means; and a plurality of interchangeable object removal tools having shafts for releasable attachment with said nose member opening.

* * * * *